(12) United States Patent
Lee et al.

(10) Patent No.: US 10,088,435 B2
(45) Date of Patent: Oct. 2, 2018

(54) DETECTION DEVICE FOR TURBOMACHINE SYSTEM

(71) Applicant: LG ELECTRONICS INC., Seoul (KR)

(72) Inventors: Kiwook Lee, Seoul (KR); Chanmyung Park, Seoul (KR); Namsoo Lee, Seoul (KR); Jinhee Jeong, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 15/470,108

(22) Filed: Mar. 27, 2017

(65) Prior Publication Data

US 2017/0276616 A1    Sep. 28, 2017

(30) Foreign Application Priority Data

Mar. 28, 2016  (KR) ......................... 10-2016-0036857

(51) Int. Cl.
*G01N 21/00* (2006.01)
*G01N 21/954* (2006.01)
*F25B 31/02* (2006.01)
*F25B 39/00* (2006.01)
*F25B 49/02* (2006.01)
*G01M 15/14* (2006.01)
(Continued)

(52) U.S. Cl.
CPC ......... *G01N 21/954* (2013.01); *F25B 31/026* (2013.01); *F25B 39/00* (2013.01); *F25B 49/02* (2013.01); *G01M 15/14* (2013.01); *F25B 39/02* (2013.01); *F25B 39/04* (2013.01); *F25B 45/00* (2013.01); *F25B 2339/0242* (2013.01); *F25B 2339/046* (2013.01); *F25B 2345/001* (2013.01); *F25B 2345/006* (2013.01); *F25B 2500/06* (2013.01); *F25B 2500/222* (2013.01); *G01N 2021/9546* (2013.01)

(58) Field of Classification Search
CPC .. G01N 21/8806; G01N 25/72; G01N 21/954; G01N 27/902; G01N 21/95; G01N 21/9515; G01N 21/95692; G01N 2223/63; G01N 21/8851; G01N 2291/2693; G01N 23/046; G01N 3/00; G01N 21/55; G01N 21/8422
See application file for complete search history.

(56) References Cited

U.S. PATENT DOCUMENTS 5,102,221 A * 4/1992 Desgranges ........... B23Q 5/027
                                                    356/241.1
5,335,061 A * 8/1994 Yamamoto ............ G01M 15/10
                                                    356/241.1
(Continued)

FOREIGN PATENT DOCUMENTS

GB          2425764 A  * 11/2006
JP          2011-132953 A    7/2011

*Primary Examiner* — Michael P Stafira
(74) *Attorney, Agent, or Firm* — Birch, Stewart, Kolasch & Birch, LLP

(57) ABSTRACT

Disclosed is a detection device for detecting a turbomachine including an opening, the detection device comprises: a flange configured to close the opening; and an endoscope assembly including an endoscope body, a detector extending from the endoscope assembly and inserted into an internal space of the turbomachine through the flange and an extension part connecting the endoscope body and the detector.

15 Claims, 13 Drawing Sheets

(51) Int. Cl.
   *F25B 39/02*   (2006.01)
   *F25B 39/04*   (2006.01)
   *F25B 45/00*   (2006.01)

(56) References Cited

U.S. PATENT DOCUMENTS

| | | | | |
|---|---|---|---|---|
| 5,575,754 | A | * | 11/1996 | Konomura ............. G01B 11/02 356/241.6 |
| 6,011,617 | A | * | 1/2000 | Naudet ............. G02B 23/2492 356/237.1 |
| 2005/0200842 | A1 | * | 9/2005 | Bonningue ............ G01N 21/91 356/241.1 |
| 2007/0132840 | A1 | * | 6/2007 | Konomura ........... G01N 21/954 348/65 |
| 2009/0027665 | A1 | * | 1/2009 | Ogburn ............. G02B 23/2484 356/241.1 |
| 2009/0079821 | A1 | * | 3/2009 | Bousquet ............ A61B 1/0055 348/65 |
| 2011/0018530 | A1 | * | 1/2011 | Bousquet ........... G01N 27/9033 324/240 |
| 2016/0178532 | A1 | * | 6/2016 | Lim ................... G01N 21/8851 348/46 |
| 2016/0194088 | A1 | * | 7/2016 | Leutard ................ F01D 21/003 415/118 |
| 2017/0074120 | A1 | * | 3/2017 | Drouin .................. F01D 21/003 |
| 2017/0261399 | A1 | * | 9/2017 | Almstedt ................ G01M 7/08 |

* cited by examiner

DETECTION DEVICE FOR TURBOMACHINE SYSTEM

CROSS-REFERENCE TO RELATED APPLICATIONS

The present application claims priority under 35 U.S.C. 119 and 35 U.S.C. 365 to Korean Patent Application No. 10-2016-0036857 (filed on Mar. 28, 2016), which is hereby incorporated by reference in its entirety.

TECHNICAL FIELD

The present invention relates to a detection device for a turbomachine system.

BACKGROUND

A turbomachine system refers to a system for compressing working fluid (e.g., air or refrigerant) or increasing a flow rate of working fluid using a turbomachine such as a turbo compressor, a turbo blower or a turbo fan.

In a conventional turbomachine, high-speed rotation was implemented using a multiplying gear in a motor rotating at a constant speed. However, recently, with development of related technologies such as bearings and invertors, direct connection type high-speed rotation technology for direct connection to a motor has been applied.

The turbomachine needs to pre-diagnose potential cracks to prevent damage or failure of a system.

The following related art was disclosed.

Japanese Patent Laid-Open Publication No. 2011132953 (2011.7.7)

Title of the Invention: Method and system for detecting cracks of turbomachine blade In the related art, a method of mounting a GAP sensor inside a turbomachine or mounting an acoustic sensor or an acceleration sensor outside the turbomachine and determining that abnormality occurs when a signal detected by the sensor is out of an allowable range and a system using the same are disclosed.

This method and system can pre-diagnose failure such as potential cracks but cannot determine an accurate position of failure or a degree of failure.

Accordingly, in order to directly determine a state of failure such as a position of failure or a degree of failure, the turbomachine should be necessarily stopped and disassembled.

Since it takes considerable labor and time to disassemble a turbomachine having a medium to large size to find a position of failure, cost and time problems occur.

Accordingly, there is a need for a detection device capable of accurately and directly determining a position of failure and a degree of failure

SUMMARY

An object of the present invention is to provide a detection device capable of directly observing a position and degree of failure.

Another object of the present invention is to provide a detection device capable of observing an internal space of a turbomachine even during operation of the turbomachine.

In one embodiment, A detection device for detecting a turbomachine including an opening, the detection device comprises: a flange configured to close the opening; and an endoscope assembly including an endoscope body, a detector extending from the endoscope assembly and inserted into an internal space of the turbomachine through the flange and an extension part connecting the endoscope body and the detector.

DETAILED DESCRIPTION OF THE EMBODIMENTS

Hereinafter, specific embodiments will be described with reference to accompanying drawings. It will be understood that the description herein is not intended to limit the claims to the specific embodiments described. On the contrary, it is intended to cover alternatives, modifications, and equivalents as may be included within the spirit and scope of the present disclosure as defined by the appended claims.

Figure 1:
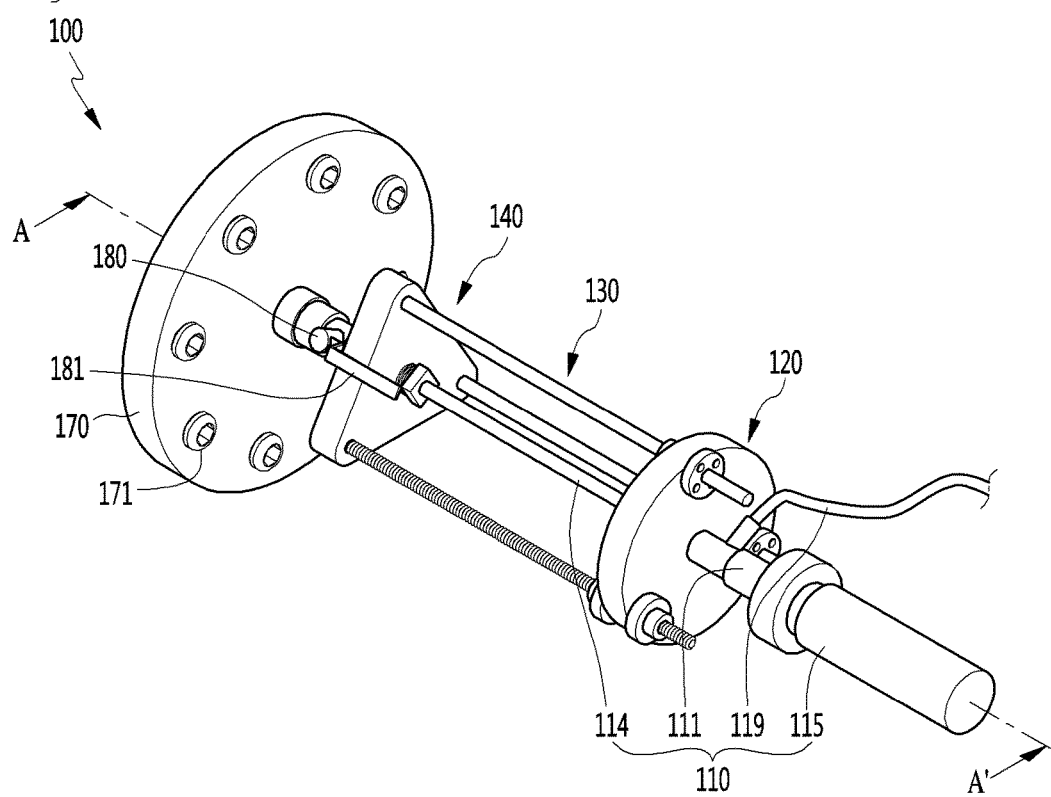
FIG. 1 is a perspective view of a detection device according to an embodiment of the present invention.
Figure 2:
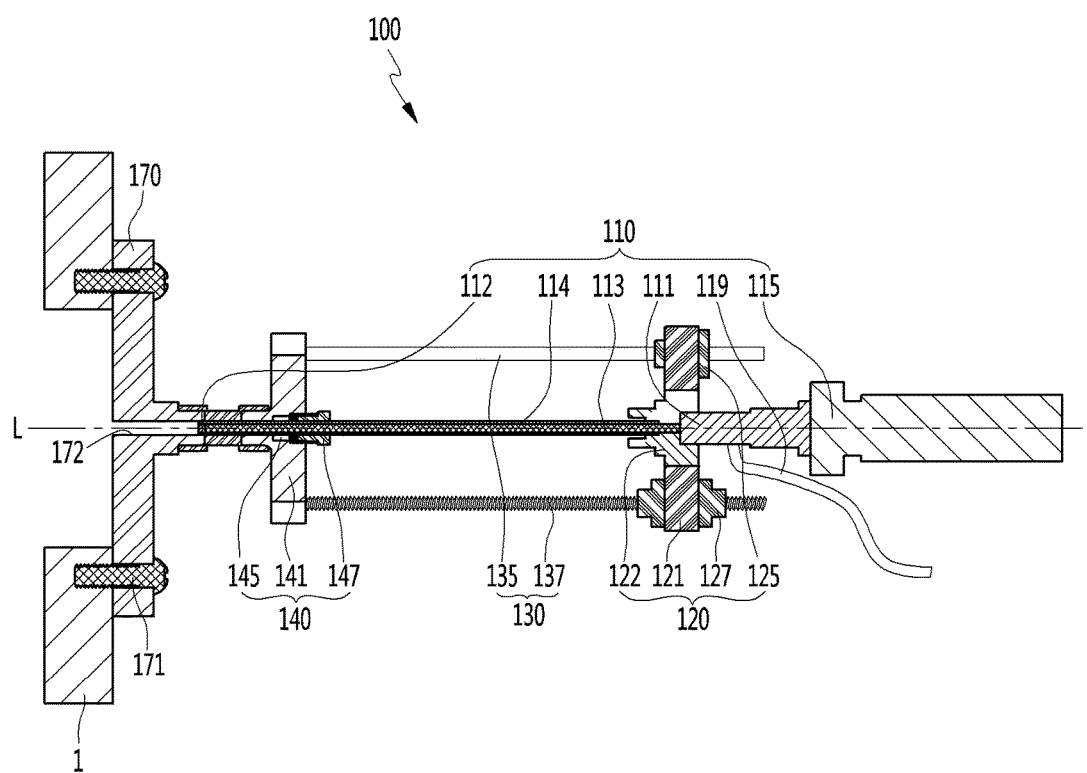
FIG. 2 is a cross-sectional view taken along line A-A of FIG. 1.
Figure 3:
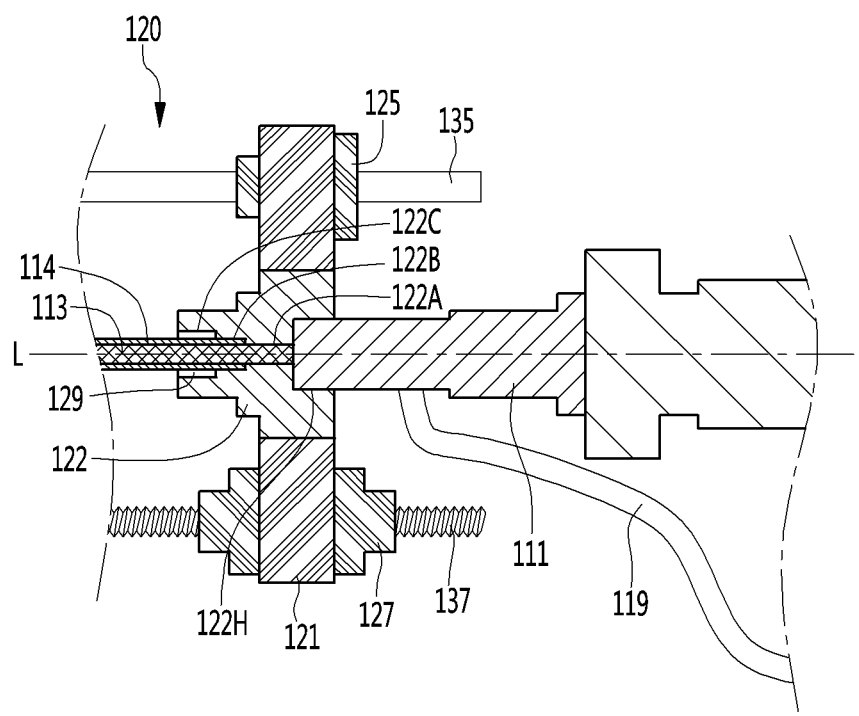
FIG. 3 is a cross-sectional view of a mounting assembly according to an embodiment of the present invention.
Figure 4:
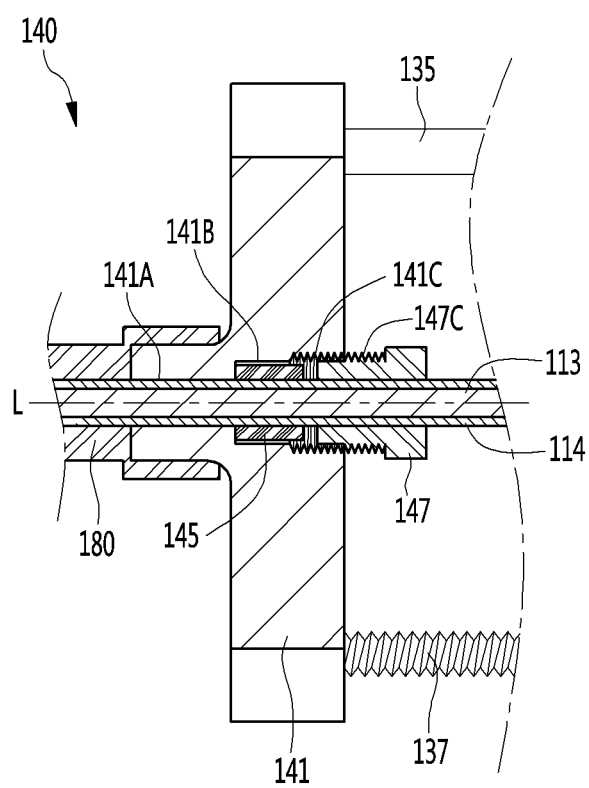
FIGS. 4 and 5 are cross-sectional views of a fixing assembly according to an embodiment of the present invention.
Figure 5:
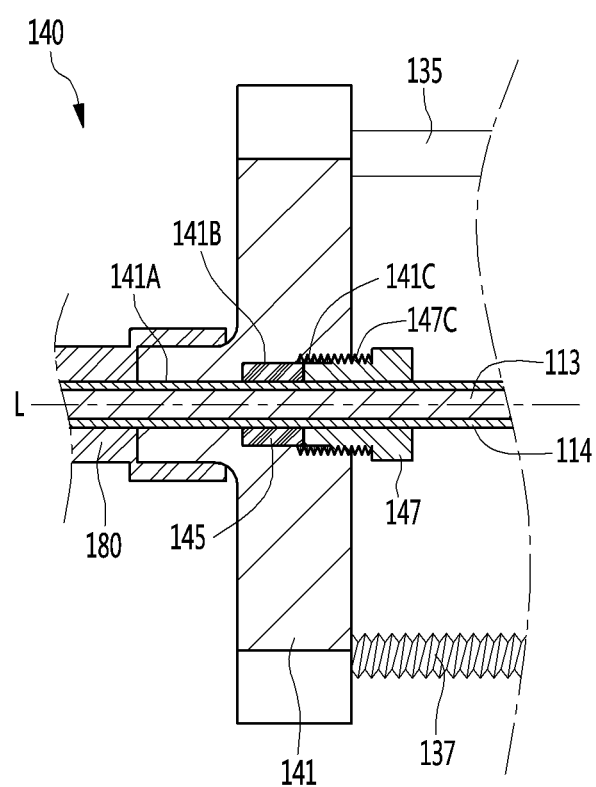

FIG. 1 is a perspective view of a detection device according to an embodiment of the present invention, FIG. 2 is a cross-sectional view taken along line A-A of FIG. 1, FIG. 3 is a cross-sectional view of a mounting assembly according to an embodiment of the present invention, and FIGS. 4 and 5 are cross-sectional views of a fixing assembly according to an embodiment of the present invention.

Referring to FIGS. 1 to 5, the detection device 100 according to the embodiment of the present invention includes an endoscope assembly 110 for detecting an internal space of a turbomachine, a mounting assembly 120, in which the endoscope assembly 110 is mounted such that the endoscope assembly 110 is not pushed backward by pressure of the internal space, a support assembly 130 supporting the mounting assembly 120 such that the mounting assembly 120 is spaced apart from the turbomachine by a predetermined distance, and a fixing assembly 140 fastened to the support assembly 130 to fix the support assembly 130 to the turbomachine.

The endoscope assembly 110 includes an endoscope body 111, a detector 112 inserted into the turbomachine and a connector 113 for connecting the endoscope body 111 and the detector 112.

An optical device such as a camera may be mounted in the detector 112 to detect the internal state of the turbomachine through the optical device. For example, the inner wall of the turbomachine may be detected and whether the inner wall is cracked and a degree of crack may be detected. The detector 112 may include a lens (not shown) capable of changing the detection range of the detector. The detector 112 may detect the front side and the lateral side of the detector 112 through the lens.

The connector 113 may extend from the endoscope body 111 to the detector 112. For example, the connector 113 may extend in a front-and-rear direction. At this time, the front-and-rear direction means a direction from the mounting assembly 120 to the fixing assembly 140. That is, the detector 112 may be disposed at one end of the connector 113 and the endoscope body 111 may be connected to the other end of the connector 113.

The endoscope assembly 110 may further include an insertion pipe 114 for preventing the connector 113 from being bent in one direction. The insertion pipe 114 may extend in the extension direction of the connector 113. That is, the insertion pipe 114 may extend in the front-and-rear direction. The insertion pipe 114 may be formed to surround and fix the outer circumferential surface of the connector 113. From a different point of view, the insertion pipe 114 may have a hole corresponding to the outer diameter of the connector 113 and the connector 113 may be inserted into the hole of the insertion pipe 114.

Although the insertion pipe 114 is formed separately from the connector 113 in the present embodiment, the present invention is not limited thereto and the insertion pipe 114 may be formed integrally with the connector 113. Since the insertion pipe 114 prevents the connector 113 from being bent by fluid flowing in the internal space of the turbomachine, it is possible to prevent the detection range of the detector 112 from being unintentionally changed.

The endoscope assembly 110 may further include a knob 115 capable of moving the endoscope body 111. For example, a user may move the knob 115 in the front-and-rear direction to move the endoscope body 111 in the front-and-rear direction. The endoscope body 111 may be moved forward by movement of the knob 115. At this time, portions of the detector 112 and the connector 113 may be inserted into the internal space of the turbomachine.

The endoscope assembly 110 may further include a cable 119 for connecting the endoscope body 111 and an external device (not shown) and delivering information detected by the detector 112 to the external device. Through the external device, the user may check the state of the internal space of the turbomachine detected by the detector 112. For example, the external device may include a display device.

The mounting assembly 120 includes a mounting assembly body 121 and an accommodation part 122 provided at one side of the mounting assembly body 121 to accommodate the endoscope body 111. For example, the mounting assembly body 121 may be provided to face one surface of the turbomachine and may be formed in a disk shape.

In addition, the accommodation part 122 may be provided at the center of the mounting assembly 120. The accommodation part 122 may include a fastener 122H opened backward and one side of the endoscope body 111 may be fastened to the fastener 122H. For example, the accommodation part 122 may include a fastener 122H formed by recessing a rear surface thereof. That is, the accommodation part 122 may include the fastener 122H having a first recessed surface formed by recessing one surface of the accommodation part 122. At this time, the connector 113 extending from one side of the endoscope body 111 may penetrate through the accommodation part 122.

The accommodation part 122 may include a first penetration part 122A, through which the connector 113 penetrates. The penetration part may be formed in the first recessed surface and the first penetration part 122A may have a size corresponding to the diameter of the connector 113 and the first penetration part 122A penetrates through the accommodation part 122 in the front-and-rear direction.

Accordingly, one side of the endoscope body 111 is fastened to the fastener 122H and a portion of the outer circumferential surface of the connector 113 closely contacts the first penetration part 122A, such that the endoscope assembly 110 is fixed to the mounting assembly 120.

In addition, the accommodation part 122 may further include a first fixing part 122B having a second recessed surface formed by recessing the front surface thereof backward by a predetermined depth. The first fixing part may be centered on the first penetration part and a virtual extension L. For example, the first fixing part 122B may be provided at the front side of the first penetration part 122A.

The first fixing part 122B may have a size corresponding to the diameter of the insertion part 114. One side of the insertion pipe 114 is inserted into the first fixing part 122B. At this time, the connector 113 penetrating through the first penetration part 122A in the endoscope body 111 is accommodated in the insertion pipe 114. That is, a portion of the extension part 113 is fixed to the first penetration part 122A and the other portion of the extension part 113 may be inserted into the insertion pipe 114 fixed to the first fixing part 122B.

The diameter of the first fixing part 122B is greater than that of the first penetration part 122A. For example, the diameter of the first fixing part 122B may be greater than that of the first penetration part 122A by the thickness of the insertion pipe 114.

A step difference may be formed at the boundary between the first fixing part 122B and the first penetration part 122A and the height thereof may correspond to the thickness of the insertion pipe 114. In addition, the step difference may contact one end of the insertion pipe 114. Accordingly, the insertion pipe 114 is inserted into the first fixing part 122B such that one end of the insertion pipe 114 contacts the step difference.

In addition, the accommodation part 122 includes a first sealing member 129 for preventing fluid leakage and a first sealing part 122C forming a space, into which the first sealing member 129 is inserted. The first sealing part 122C may include a third recessed surface formed by recessing the front surface of the accommodation part 112 backward by a predetermined distance.

The sealing part 122C may be centered on the virtual extension L. For example, the first sealing part 122C may be formed at the front side of the first fixing part 122B.

The diameter of the first sealing part 122C is greater than that of the first penetration part 122A or the second penetration part 122B. At this time, the first sealing member 129 is inserted into a space between the outer circumferential surface of the insertion pipe 114 and the inner circumferential surface of the first sealing part 122C. The first sealing member 129 prevents refrigerant permeated into the accommodation part 122 from being moved out of the mounting assembly 120 through the insertion pipe 114.

At this time, the first penetration part 122A, the first fixing part 122B and the first sealing part 122C may be aligned on the virtual extension L. The extension L penetrates through the center of the accommodation part 122 and the center of the fixing assembly 140. Accordingly, the first penetration part 122A, the first fixing part 122B, the first sealing part 122C and the fastener 122H may be formed at the center of the accommodation part 122. The virtual extension L may be understood as the central axis of the detection device 100.

The mounting assembly 120 further includes a ball bush 125 provided at the edge of the mounting assembly body 121. The ball bush 125 is coupled to a bar 135 to guide movement of the mounting assembly 120 in the front-and-rear direction. In addition, a plurality of ball bushes 125 may be provided to correspond to the bar 135.

In addition, the mounting assembly 120 further includes a ball spline 127 provided at the edge of the mounting assembly body 121. The ball spline 127 is coupled to a screw 137 such that the mounting assembly 120 is spaced apart from the fixing part 130 by a predetermined distance. The ball bush 125 and the ball spline 127 may penetrate through the edge of the mounting assembly body 121.

The support assembly 130 connects the mounting assembly 120 and the fixing assembly 140. For example, the support assembly 130 is fastened to the fixing assembly 140 to support the mounting assembly 120.

The support assembly 130 includes the bar 135 extending from the fixing assembly 140 to the mounting assembly 120. The bar 135 extends in the front-and-rear direction and may be coupled to the ball bush 125. The ball bush 125 may slide on the outer circumferential surface of the bar 125 and the mounting assembly 120 may be moved along the bar 125 in the front-and-rear direction.

The support assembly 130 may include the screw 137 including a thread. The screw 127 extends in the front-and-rear direction and may be coupled to the ball spline 127. The ball spline 127 may be fastened to the thread provided in the screw 127 to restrict movement of the mounting assembly 120 in the front-and-rear direction.

That is, the ball spline 127 may be moved along the screw 137 and the mounting assembly 120 may be moved in the front-and-rear direction. The ball spline 127 may be fixed to one point of the screw 137 to restrict movement of the mounting assembly 120 in the front-and-rear direction. The bar 135 and the screw 137 may be provided to be symmetrical to each other with respect to the insertion pipe 114.

The fixing assembly 140 includes a fixing assembly body 141, to which the support assembly 130 is fastened. The fixing assembly body 141 may be provided to face the mounting assembly body 121 and may be spaced apart from the mounting assembly body 121 by a predetermined distance by the support assembly 120.

The support assembly 130 may be fastened to the edge of the fixing assembly body 141. For example, the fixing assembly body 141 may be configured in an approximately triangular shape when viewed from the front side of the mounting assembly 120 and the support assembly 130 may be fastened to the vertex of the triangle. For example, the bar 135 may be fastened to the two vertexes of the triangle and the screw 137 may be fastened to the remaining vertex of the triangle. At this time, the insertion pipe 114 penetrates through the center of the triangle.

A second penetration part 141A, through which the insertion pipe 114 penetrates, is provided at the center of the fixing assembly body 141. For example, the second penetration part 141A is formed at the center of the fixing assembly body 141. In addition, the diameter of the second penetration part 141A may correspond to the diameter of the insertion pipe 114.

The second penetration part 141A may be provided to correspond to the first fixing part 122B. That is, the center of the first fixing part 122B and the center of the second penetration part 141A may be aligned on the virtual extension L. Accordingly, one side of the insertion pipe 114 may be fixed to the first fixing part 122B and the other end of the insertion pipe 114 may be fixed to the second penetration part 141A.

One end of the insertion pipe 114 is in contact with and supported by the step difference formed at the boundary between the first fixing part 122B and the first penetration part 122A, such that the insertion pipe 114 cannot penetrate through the mounting assembly 120. However, the other end of the insertion pipe 115 is not fixed by the step difference to be moved in the front-and-rear direction of the fixing assembly 140.

The fixing assembly 140 includes a second sealing part 141B having a fourth recessed surface formed by recessing the rear surface of the fixing assembly body 141 forward by a predetermined depth. The diameter of the second sealing part 141B may be greater than that of the second penetration part 141A and the second sealing part 141B includes a cylindrical hole centered on the second penetration part 141A. The second sealing part 141B may be aligned on the virtual extension L.

The second sealing member 145 may be inserted into the second sealing part 141B. The second sealing member 145 may be formed to correspond to the second sealing part 141B. For example, the second sealing member 145 may have an inner circumferential surface and an outer circumferential surface formed in a ring shape. The inner circumferential surface may contact the outer circumferential surface of the insertion pipe 114 and the outer circumferential surface may contact the inner circumferential surface of the second sealing member 145.

A screw part 141C is provided in the inner circumferential surface of the second sealing part 141B. For example, the screw part 141C may be provided at the rear side of the second sealing part 141B and the screw part 141C includes a female thread.

The fixing assembly 140 may further include a thread fastener 147 inserted into the second sealing part 141B. The thread fastener 147 may be formed such that the insertion pipe 114 penetrates therethrough. For example, the insertion pipe 114 may penetrate through the center of the thread fastener 147.

Accordingly, the thread fastener 147 may be moved along the outer circumferential surface of the insertion pipe 114 in the front-and-rear direction. In contrast, the insertion pipe 114 may be moved in the front-and-rear surface in a state of penetrating through the thread fastener 147.

The size of the outer circumferential surface of the thread fastener 147 may correspond to the diameter of the inner circumferential surface of the second sealing part 141B. A screw part 147C may be provided on the outer circumferential surface of the thread fastener 147. For example, the screw part 147C may include a male thread.

The screw part 147C of the thread fastener is fastened to the thread 141C of the second sealing part. That is, the thread fastener 147 moves forward along the thread 141C while rotating in one direction and moves backward along the thread 141C while rotating in another direction.

When the thread fastener 147 is fastened to the second sealing part 141B, the second sealing member 145 provided in the second sealing part 141B may be compressed by the thread fastener 147 in the front-and-rear direction.

The second sealing member 145 may be made of a soft material and the length thereof in an axial direction may be decreased and the length thereof in a radial direction may be increased upon being compressed in the front-and-rear direction. When the length of the second sealing member 145 in the radial direction is increased, the outer circumferential surface of the second sealing member 145 and the inner circumferential surface of the second sealing part 141B closely contact each other and the inner circumferential surface of the second sealing member 145 and the outer circumferential surface of the insertion pipe 114 closely contact each other. Accordingly, sealing is performed in the first penetration hole 122A.

When the thread fastener 147 moves toward the inside of the second sealing part 141A, the second sealing member 145 seals the first penetration hole 122A (see FIG. 5). In contrast, when the thread fastener 148 moves toward the outside of the second sealing part 141B, sealing of the first penetration hole 122A is gradually released (see FIG. 4).

The user may move the thread fastener 147 backward by a predetermined distance and then move the insertion pipe 114 in the front-and-rear direction. When the position of the endoscope assembly is fixed, the thread fastener 147 may be moved forward to perform sealing. Movement of the endoscope assembly 110 will be described below in detail.

The second sealing member 145 prevents refrigerant from flowing into the fixing assembly 140 and the first sealing member 129 prevents refrigerant from flowing into the mounting assembly 120.

The detection device 100 may further include a flange for closing an opening of the turbomachine. The flange 170 may be formed in a shape corresponding to the opening of the turbomachine. For example, the flange may be formed in a circular shape.

The flange 170 may be fastened to the edge of the opening by the fastening member 171. The center of the flange 170 may include a third penetration part 172, through which the flange 170 penetrates (see FIG. 7). At this time, the first penetration part 122A, the second penetration part 141A and the third penetration part 172 may be aligned on the virtual extension L.

The second penetration part 141A and the third penetration part 172 may be understood as a channel because the extension part 113 and the insertion pipe 114 may be moved in the front-and-rear direction according to the position of the mounting assembly 120.

The detection device 100 may be provided between the flange 170 and the fixing assembly 140 and may further include a valve 180 for selectively blocking the channel of the endoscope assembly 110. Since the valve 180 blocks the channel when the detection device 100 is not used, it is possible to prevent refrigerant from flowing from the internal space. The valve 180 may include a knob 181 for opening and closing the valve.

Hereinafter, a process of inserting the detection device 100 into the turbomachine will be described.

Figure 6:
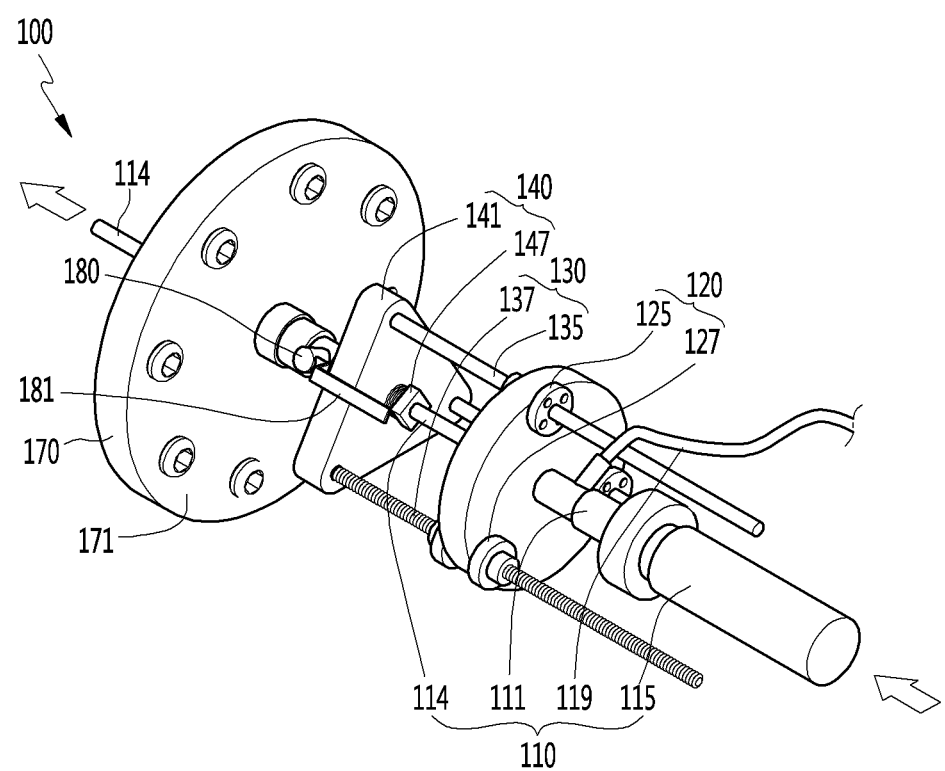
FIGS. 6 and 7 are views showing a state in which a detection device of the present invention is inserted into an internal space of a turbomachine.
Figure 7:
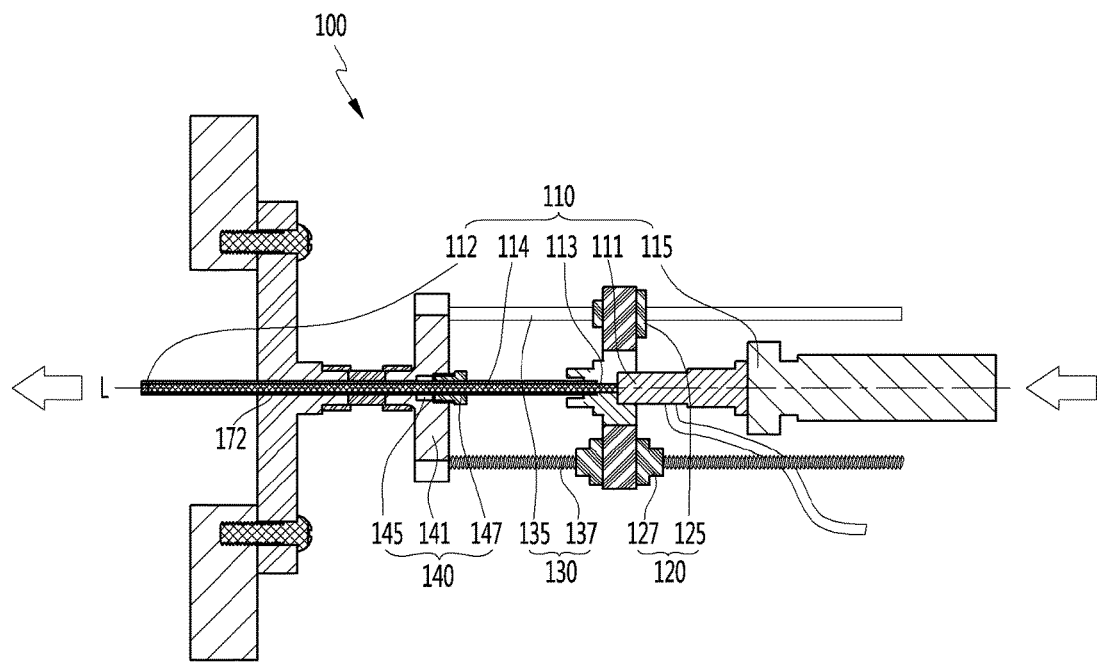

FIGS. 6 and 7 are views showing a state in which a detection device of the present invention is inserted into an internal space of a turbomachine.

Referring to FIGS. 6 and 7, first, the valve 180 is opened to open the channel connecting the second penetration part 141A and the third penetration part 172. Fixing of the ball spline 127 is released such that the mounting assembly 120 is moved along the support assembly 130.

The endoscope assembly 110 is pushed toward the turbomachine. At this time, the endoscope body 111 is moved forward in a state of being mounted in the mounting assembly 120. The mounting assembly 120 is moved toward the fixing assembly 140.

At this time, the extension part 113 and the insertion pipe 114 are moved along the second penetration part 141A to penetrate through the fixing assembly 140 and the third penetration part 173, thereby being inserted into the internal space of the turbomachine.

When movement of the endoscope assembly is completed, the ball spline 127 is fixed to the screw 137 and the mounting assembly 120 is fixed so as not to be pushed backward. In addition, the thread fastener 147 rotates in one direction to pressurize the second sealing member 145.

The second sealing member 145 seals the insertion pipe 114 and the second sealing part 141B, thereby preventing refrigerant of the internal space from flowing into the fixing assembly 140.

Figure 8:
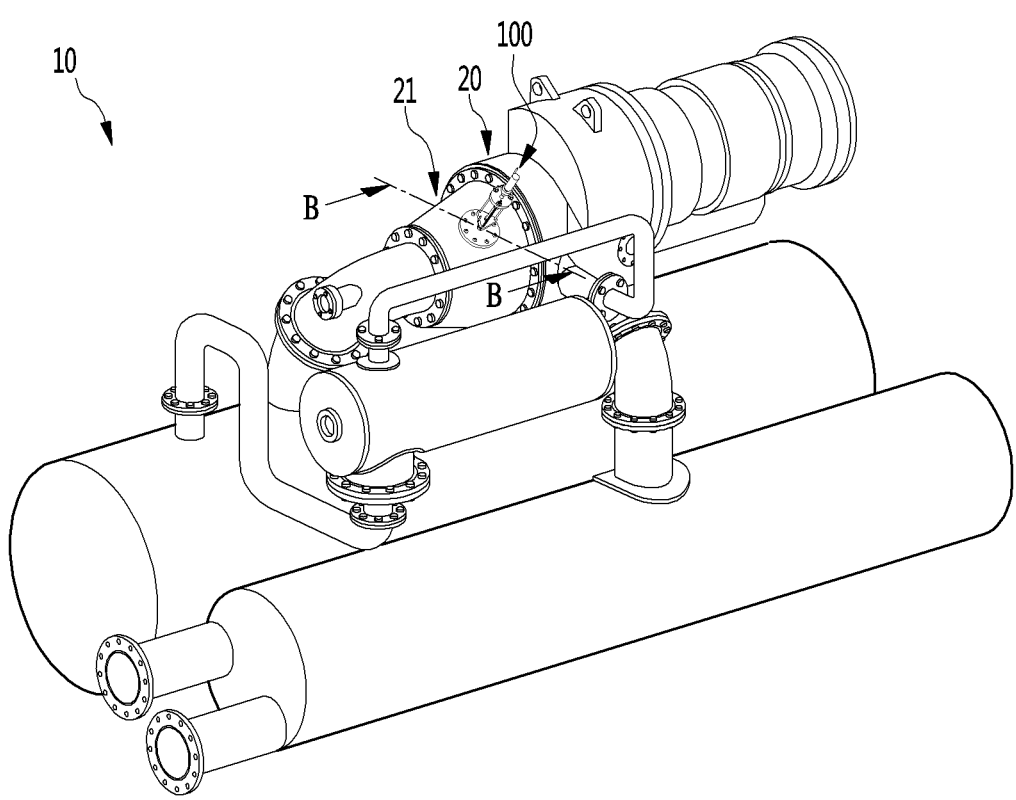
FIGS. 8 and 9 are views showing a state in which a detection device according to an embodiment of the present invention is inserted into a vane of a turbomachine.
Figure 9:
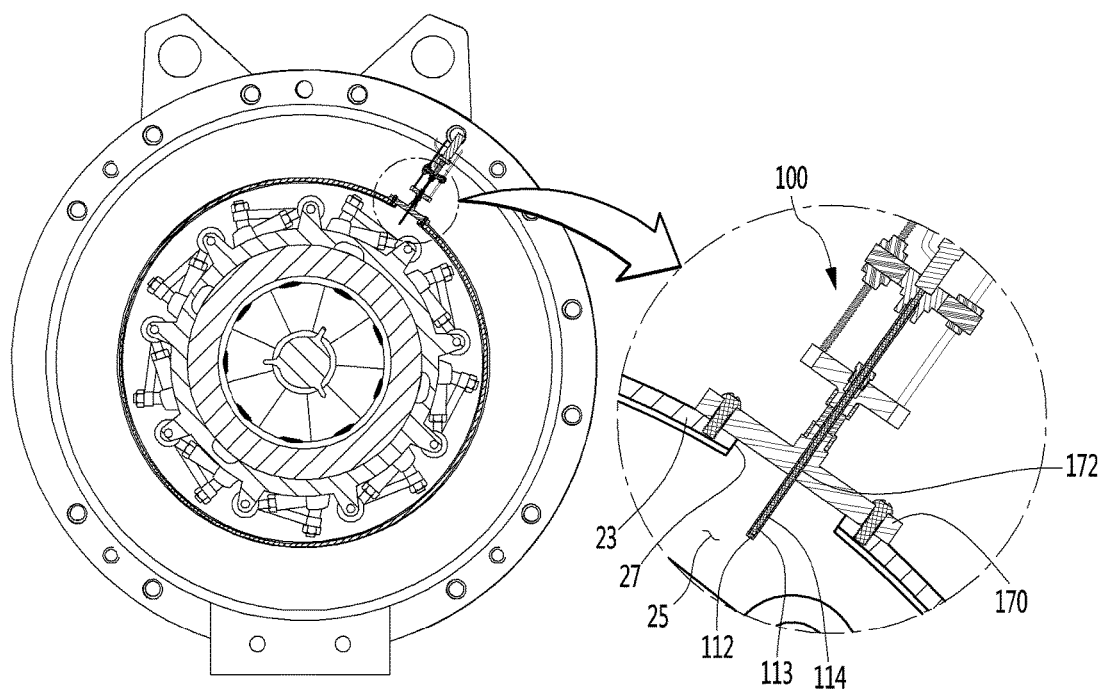

FIGS. 8 and 9 are views showing a state in which a detection device according to an embodiment of the present invention is inserted into a vane of a turbomachine.

Referring to FIGS. 8 and 9, the detection device 100 according to the embodiment of the present invention may be mounted in a compression part 20 of a chiller system 10.

The compression part 20 may include a compressor 20 for compressing refrigerant flowing in the chiller system and a vane 21 provided at the inlet side of the compressor to adjust the amount of refrigerant flowing into the compressor. The vane 21 may adjust the amount of refrigerant such that a surge voltage is not generated during operation of the compressor 20. The vane includes a shell 23 forming the appearance thereof and an internal space 25 formed in the shell 23.

An opening 27 may be formed at one side of the shell. The opening 27 may have a circular shape when viewed from the outside thereof and the flange 170 of the detection device 100 may be fastened to the edge of the opening.

The detector 112, the extension part 113 and the insertion pipe 114 of the detection device 100 may be inserted into the internal space 25 through the penetration part 172 of the flange 170 to observe the vane 28 for adjusting the amount of refrigerant or to observe the inner wall of the internal space.

Figure 10:
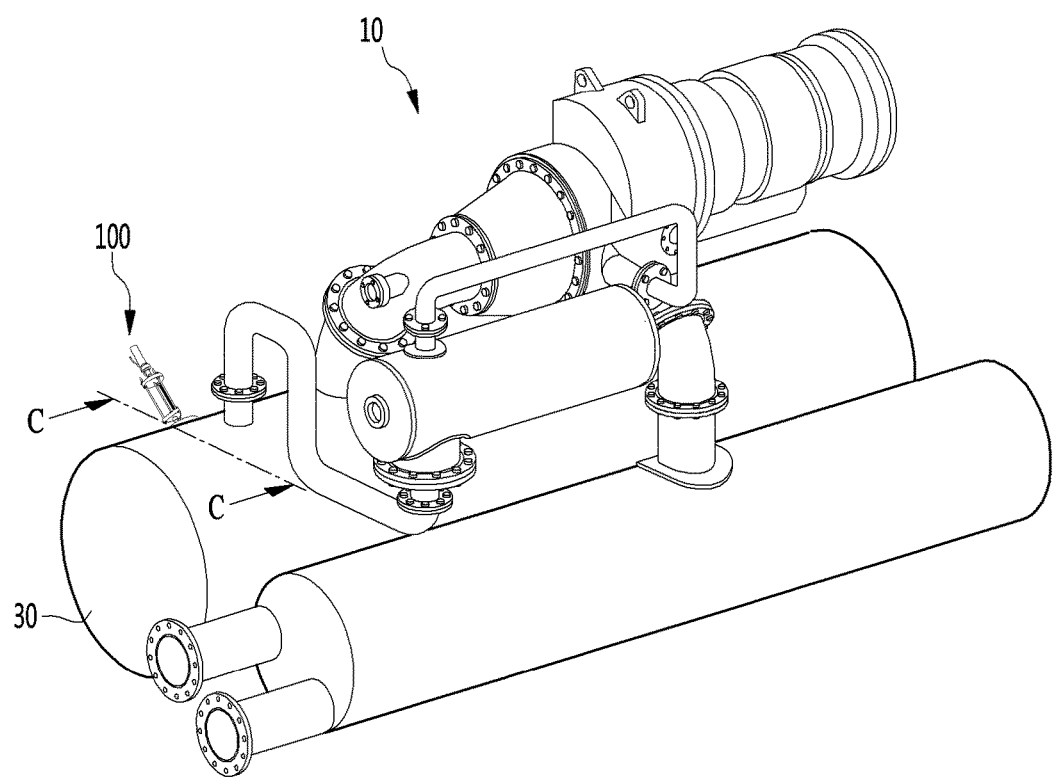
FIGS. 10 and 11 are views showing a state in which a detection device according to another embodiment of the present invention is inserted into an evaporator of a turbomachine.
Figure 11:
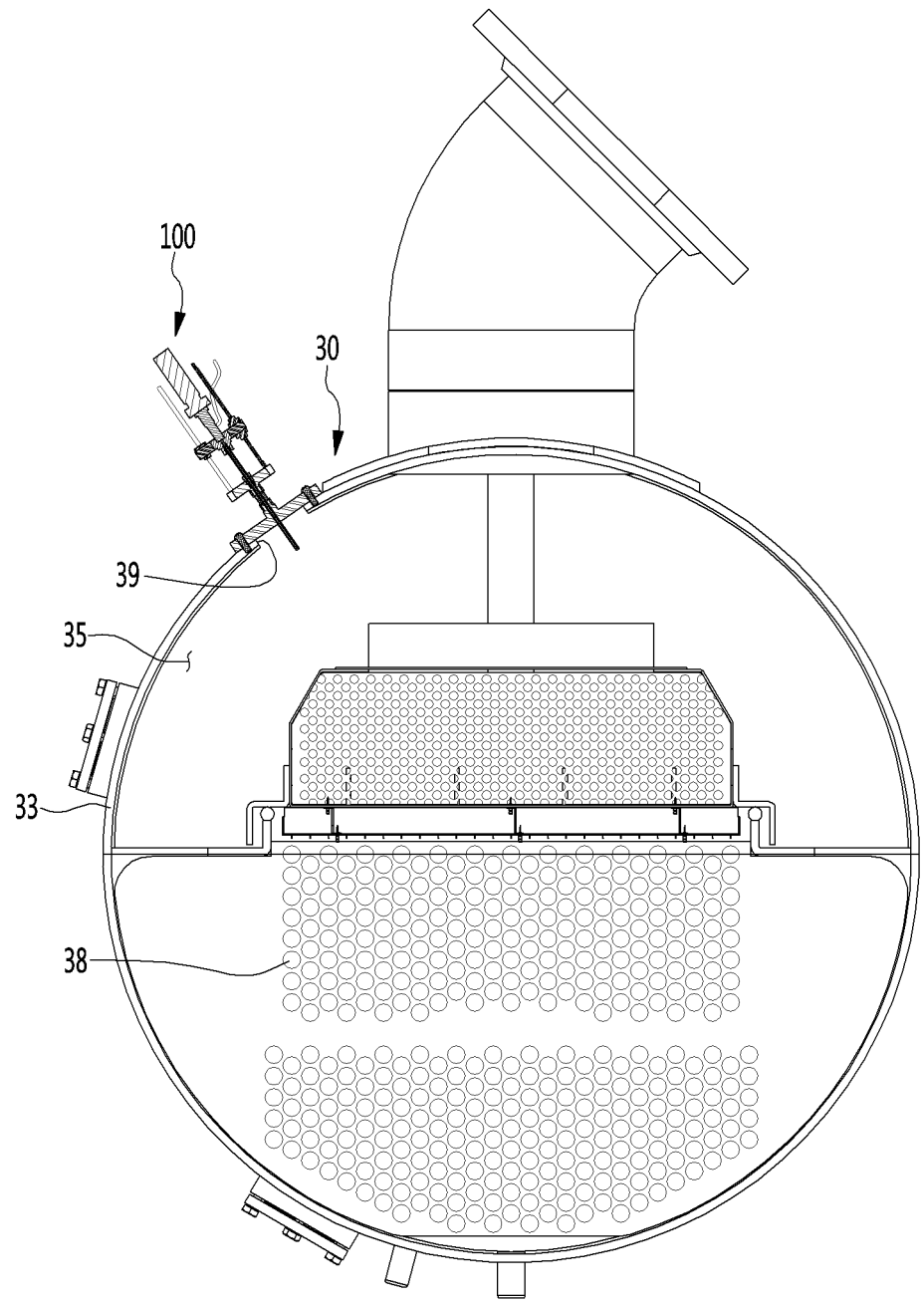

FIGS. 10 and 11 are views showing a state in which a detection device according to another embodiment of the present invention is inserted into an evaporator of a turbomachine.

Referring to FIGS. 10 and 11, the detection device 100 according to the embodiment of the present invention may be mounted in the evaporator 30 of the chiller system 10.

The evaporator 30 may be a shell-and-tube type heat exchanger and the evaporator 30 may include a shell 33 forming the appearance thereof and a cold water pipe 38 in which cold water flows. A plurality of cold water pipes 38 may be included in the shell 33.

The evaporator 30 includes an internal space 35 formed between the inner surface of the shell 33 and the outer surface of the cold water pipe 38. Refrigerant flows in the internal space 35 and refrigerant passing through the internal space 35 and cold water passing through the cold water pipe 38 exchange heat with each other. Refrigerant passing through the internal space 35 is evaporated by cold water flowing in the cold water pipe 38 and cold water is cooled by refrigerant.

The detection device 100 may be inserted into the internal space 35 to check the crack state of the inner wall of the internal space 35.

Figure 12:
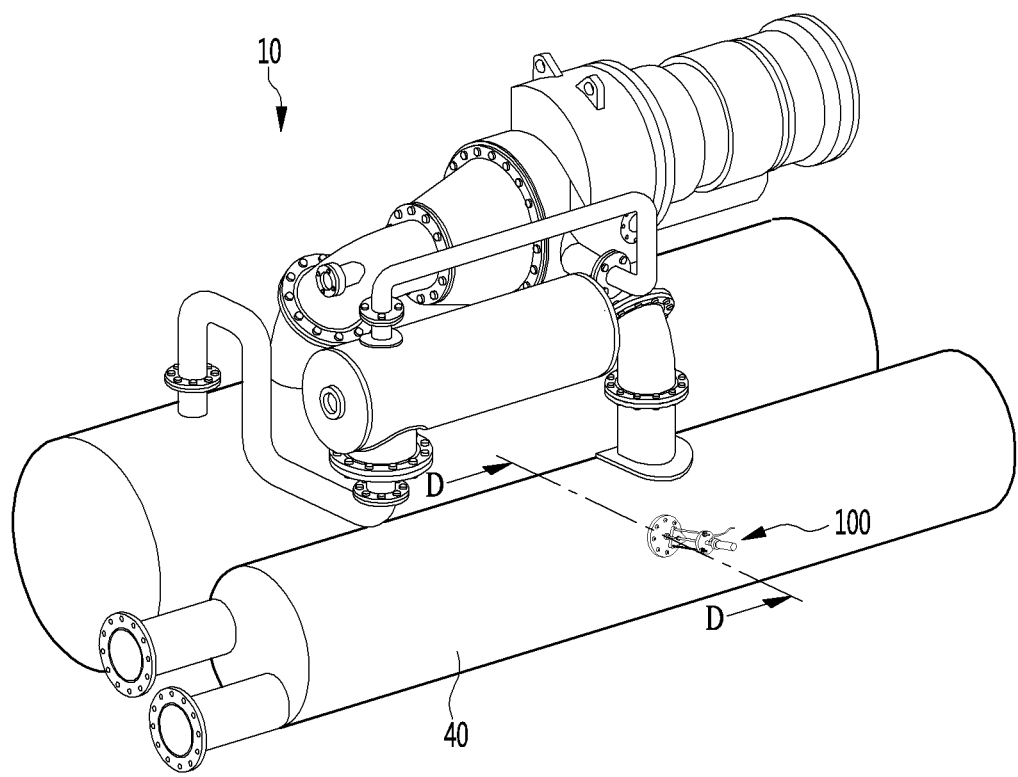
FIGS. 12 and 13 are views showing a state in which a detection device according to another embodiment of the present invention is inserted into a condenser of a turbomachine.
Figure 13:
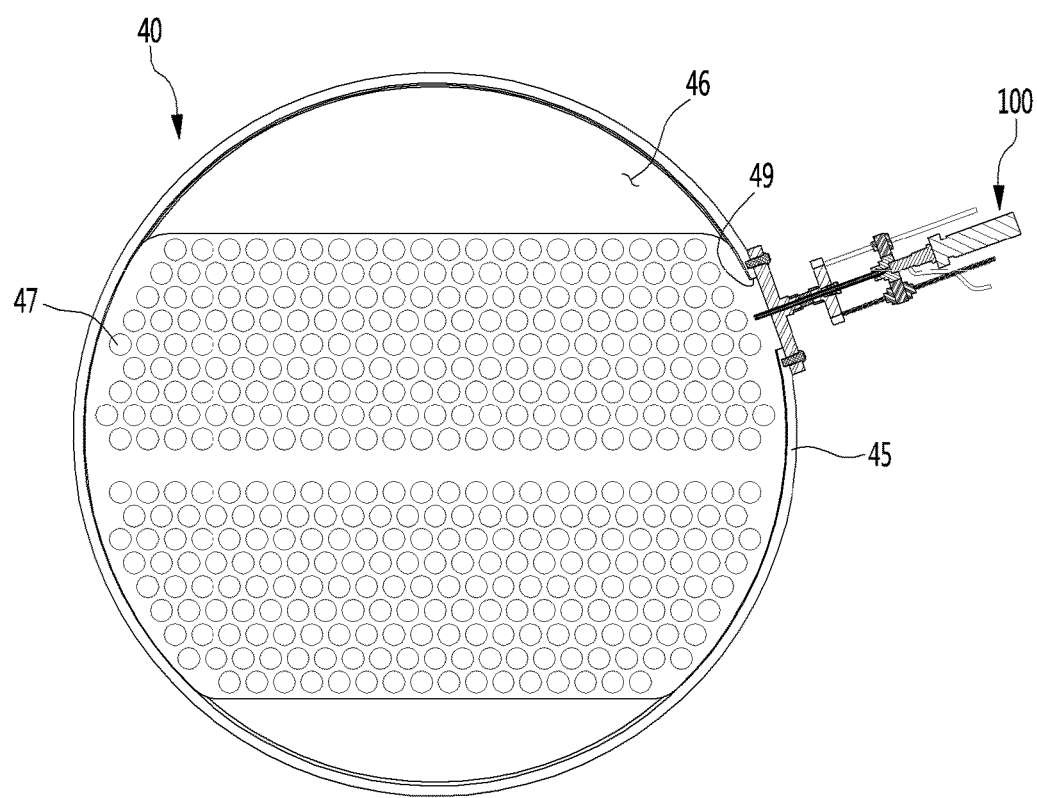

FIGS. 12 and 13 are views showing a state in which a detection device according to another embodiment of the present invention is inserted into a condenser of a turbomachine.

Referring to FIGS. 12 and 13, the condenser 40 may be a shell-and-tube type heat exchanger and the condenser 40 may include a shell 45 forming the appearance thereof and a cooling water pipe 47 in which cooling water flows.

A plurality of cooling water pipes 47 may be included in the shell 45 and the condenser 40 includes an internal space 46 formed between the inner surface of the shell 45 and the outer surface of the cooling water pipe 47.

Refrigerant flows in the internal space 46 and refrigerant passing through the internal space 46 and cooling water passing through the cooling water pipe 47 exchange heat with each other. Refrigerant passing through the internal space 46 is condensed by cooling water flowing in the cooling water pipe 47 and refrigerant is cooled by cooling water.

The detection device 100 may be inserted into the internal space 45 to check the crack state of the inner wall of the internal space 45.

Although the detection device inserted into the internal space of the chiller system is disclosed, the present invention is not limited thereto and the detection device of the present invention may be mounted in any turbomachine, the inside and outside of which are sealed. For example, the detection device of the present invention may also be mounted in an absorption refrigerator.

In addition, an object to be detected by the detection device of the present invention is not limited to the inner wall configuring the internal space, and flow of refrigerant, the speed of a rotor or vibration of a bearing may be detected according to detection purpose.

According to the embodiments, since an endoscope assembly is directly inserted into an internal space of a turbomachine, it is possible to directly check the inside of the turbomachine.

In addition, since a support assembly is included, the endoscope assembly may be inserted into the internal space without being pushed outwards by internal pressure.

In addition, since an insertion pipe supporting an extension part is included, it is possible to prevent a detection area from being unintentionally changed by fluid flowing in the internal space.

In addition, sine a first sealing member and a second sealing member are included, it is possible to prevent fluid of the internal space of the turbomachine from leaking out.

What is claimed is:

1. A detection device for detecting a turbomachine including an opening, the detection device comprising:
    a flange configured to close the opening; and
    an endoscope assembly including:
        an endoscope body;
        a detector extending from the endoscope assembly and inserted into an internal space of the turbomachine through the flange; and
        an extension part connecting the endoscope body and the detector;
    a mounting assembly in which the endoscope body is mounted, the mounting assembly including a ball bush;
    a fixing assembly spaced apart from the mounting assembly and coupled to the flange; and
    a support assembly fastened to the fixing assembly to support the mounting assembly, the support assembly including a plurality of bars mounted between the fixing assembly and the mounting assembly, the plurality of bars being configured to penetrate through the ball bush,
    wherein the ball bush is moved in a longitudinal direction of the plurality of bars, and
    wherein at least a portion of the detector and the extension part are inserted into the internal space through the fixing assembly.

2. The detection device according to claim 1, wherein:
    the support assembly includes a screw,
    the mounting assembly includes a ball spline, through which the screw penetrates, and
    the ball spline is selectively fixed to the screw to restrict movement of the mounting assembly.

3. The detection device according to claim 1, wherein the mounting assembly includes:
    a mounting assembly body;
    a fastener having a first recessed surface formed by recessing one surface of the mounting assembly body, the fastener being configured to accommodate the endoscope body; and
    a first penetration part located at the first recessed surface, the first penetration part being configured to allow the extension part to pass through the mounting assembly body.

4. The detection device according to claim 3, wherein the endoscope assembly further includes an insertion pipe provided to surround an outer circumferential surface of the extension part to prevent the extension part from being bent.

5. The detection device according to claim 4, wherein:
    the mounting assembly includes a first fixing part having a second recessed surface formed by recessing the other surface of the mounting assembly body, the first fixing part being configured to fix one side of the insertion pipe, and
    the insertion pipe is fixed to the second recessed surface of the first fixing part.

6. The detection device according to claim 5, wherein the first penetration part and the first fixing part are aligned on one virtual extension.

7. The detection device according to claim 6, wherein:
    the mounting assembly includes:
    a first sealing part having a third recessed surface formed by recessing the other surface of the mounting assembly body, the first sealing part being configured to align on the extension; and
    a first sealing member inserted into the first sealing part, and
    the first sealing member contacts an inner circumferential surface of the first sealing part and an outer circumferential surface of the insertion pipe.

8. The detection device according to claim 6, wherein:
    the fixing assembly includes a fixing assembly body and a second penetration part penetrating through the fixing assembly body and provided on the extension, and
    the other side of the insertion pipe is fixed to an inner circumferential surface of the second penetration part.

9. The detection device according to claim 8, wherein the insertion pipe passes through the second penetration part when the endoscope assembly is moved.

10. The detection device according to claim 8, wherein: the fixing assembly further includes:
    a second sealing part having a fourth recessed surface formed by recessing one surface of the fixing assembly body, the second sealing part being provided on the extension; and
    a second sealing member inserted into the second sealing part, and
    the second sealing member contacts an inner circumferential surface of the second sealing part and an outer circumferential surface of the insertion pipe.

11. The detection device according to claim 10, wherein:
    the fixing assembly further includes a thread fastener fastened to the second sealing part, and
    the thread fastener pressurizes the second sealing member when the thread fastener is inserted into the second sealing part.

12. The detection device according to claim 1, wherein the endoscope assembly further includes a lens provided at one side of the detector to change a detection range of the detector.

13. The detection device according to claim 1, wherein the flange further includes a third penetration part, through which at least a portion of the detector and the extension part penetrate.

14. The detection device according to claim 1, further comprising a valve configured to couple the flange and the fixing assembly to selectively block a channel in which the detector is moved.

15. A detection device for detecting a turbomachine including an opening, the detection device comprising:
   a flange configured to close the opening;
   an endoscope assembly including:
      an endoscope body;
      a detector extending from the endoscope assembly and inserted into an internal space of the turbomachine through the flange; and
      an extension part connecting the endoscope body and the detector, at least a portion of the detector and the extension part being inserted into the internal space;
   a mounting assembly in which the endoscope body is mounted; and
   a fixing assembly spaced apart from the mounting assembly and coupled to the flange,
   wherein the fixing assembly further includes:
      a fixing assembly body including a hole into which the extension part is penetrated, the hole having an inner circumferential surface on which a first screw part is formed;
      a sealing member inserted into the hole; and
      a movable thread fastener having a second screw part fastened to the first screw part, the thread fastener being configured to pressurize the sealing member.

* * * * *